United States Patent
D'Amore et al.

(10) Patent No.: US 9,244,087 B2
(45) Date of Patent: Jan. 26, 2016

(54) METHODS FOR USING A PIPETTING DEVICE WITH INDEPENDENTLY MOVABLE PIPETTE UNITS

(71) Applicants: Alessandro D'Amore, Wohlen (CH); Urs Knecht, Richterswil (CH); Rolf Schneebeli, Mettmenstetten (CH)

(72) Inventors: Alessandro D'Amore, Wohlen (CH); Urs Knecht, Richterswil (CH); Rolf Schneebeli, Mettmenstetten (CH)

(73) Assignee: ROCHE MOLECULAR SYSTEMS, INC., Pleasanton, CA (US)

( * ) Notice: Subject to any disclaimer, the term of this patent is extended or adjusted under 35 U.S.C. 154(b) by 0 days.

(21) Appl. No.: 14/792,155

(22) Filed: Jul. 6, 2015

(65) Prior Publication Data

US 2015/0309065 A1  Oct. 29, 2015

Related U.S. Application Data

(62) Division of application No. 14/515,668, filed on Oct. 16, 2014, now Pat. No. 9,101,922, which is a division of application No. 13/169,593, filed on Jun. 27, 2011, now Pat. No. 8,900,527.

(30) Foreign Application Priority Data

Jun. 29, 2010 (EP) .................................. 10167646.8

(51) Int. Cl.
| | | |
|---|---|---|
| B01L 3/00 | (2006.01) |
| B01L 3/02 | (2006.01) |
| G01N 1/10 | (2006.01) |
| G01N 35/10 | (2006.01) |

(52) U.S. Cl.
CPC .................................. *G01N 35/1011* (2013.01)

(58) Field of Classification Search
CPC ............ G01N 35/10; G01N 35/10002; G01N 35/1009; G01N 35/1011; G01N 35/1065; G01N 35/1067
See application file for complete search history.

(56) References Cited

U.S. PATENT DOCUMENTS

| | | | |
|---|---|---|---|
| 5,288,468 A | 2/1994 | Church et al. | |
| 5,439,649 A * | 8/1995 | Tseung et al. | 422/510 |
| 6,228,659 B1 * | 5/2001 | Kowallis et al. | 436/180 |
| 7,314,598 B2 * | 1/2008 | Nishino | 422/501 |
| 7,425,305 B2 * | 9/2008 | Itoh | 422/65 |
| 7,662,339 B2 * | 2/2010 | Mattila et al. | 422/67 |
| 7,976,794 B2 * | 7/2011 | Trump | 422/501 |
| 7,988,934 B2 * | 8/2011 | Balmer | 422/509 |
| 8,772,036 B2 * | 7/2014 | Frank et al. | 436/43 |
| 2001/0036425 A1 | 11/2001 | Gazeau et al. | |
| 2002/0051737 A1 * | 5/2002 | Sollbohmer et al. | 422/100 |
| 2002/0117013 A1 | 8/2002 | Bem | |
| 2004/0096360 A1 | 5/2004 | Toi et al. | |
| 2007/0264725 A1 | 11/2007 | Wiggli et al. | |

FOREIGN PATENT DOCUMENTS

| | | |
|---|---|---|
| EP | 1477815 A1 | 11/2004 |
| EP | 1477815 B1 | 7/2006 |

(Continued)

*Primary Examiner* — Brian R Gordon
(74) *Attorney, Agent, or Firm* — David J. Chang

(57) ABSTRACT

The invention provides for a method of pipetting samples using a pipetting device including more than one pipetting unit. Each of the pipetting units are independently movable in Y and Z directions and includes an upper and a lower frame. Two adjacent pipetting units include a module arranged in a staggered manner in either of the respective upper and lower frames.

3 Claims, 6 Drawing Sheets

(56) References Cited

FOREIGN PATENT DOCUMENTS

| | | | |
|---|---|---|---|
| EP | 2019321 | A1 | 1/2009 |
| EP | 2193848 | A1 | 6/2010 |
| WO | 2002059626 | A1 | 8/2002 |
| WO | 2006000115 | A1 | 1/2006 |
| WO | 2006047026 | A2 | 5/2006 |
| WO | 2006047026 | A3 | 5/2006 |
| WO | 2007075891 | A3 | 5/2007 |
| WO | 2007075891 | A2 | 7/2007 |

* cited by examiner

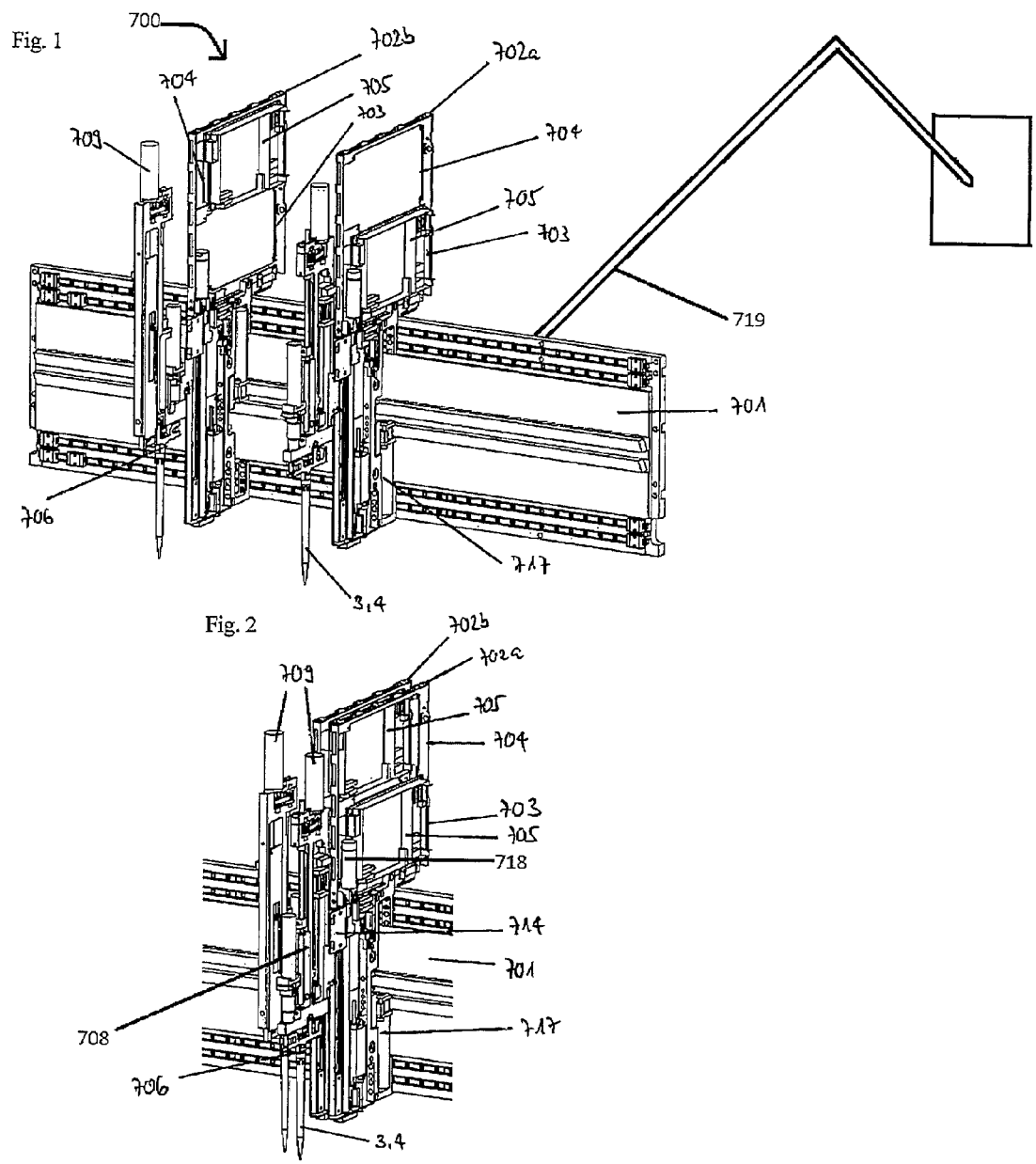

Fig. 3 a
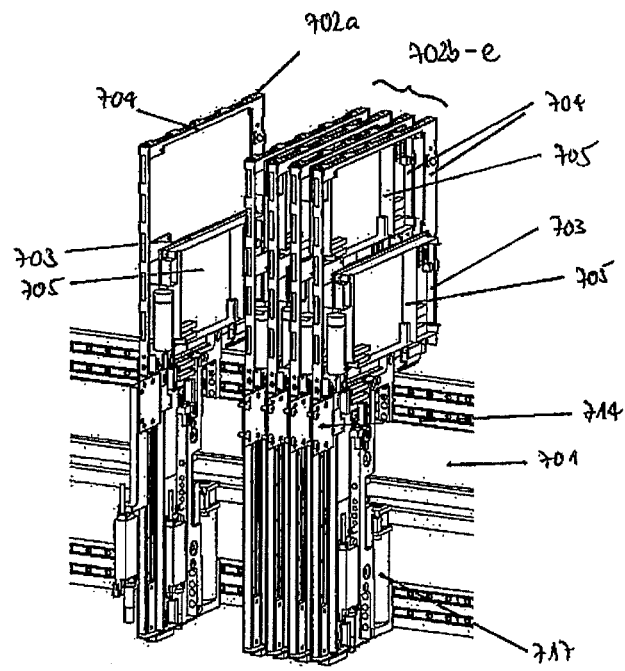
b
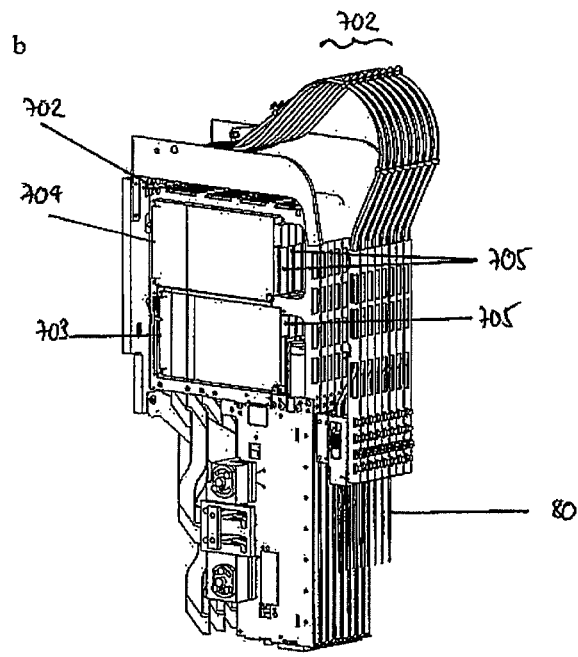

Fig. 5 a
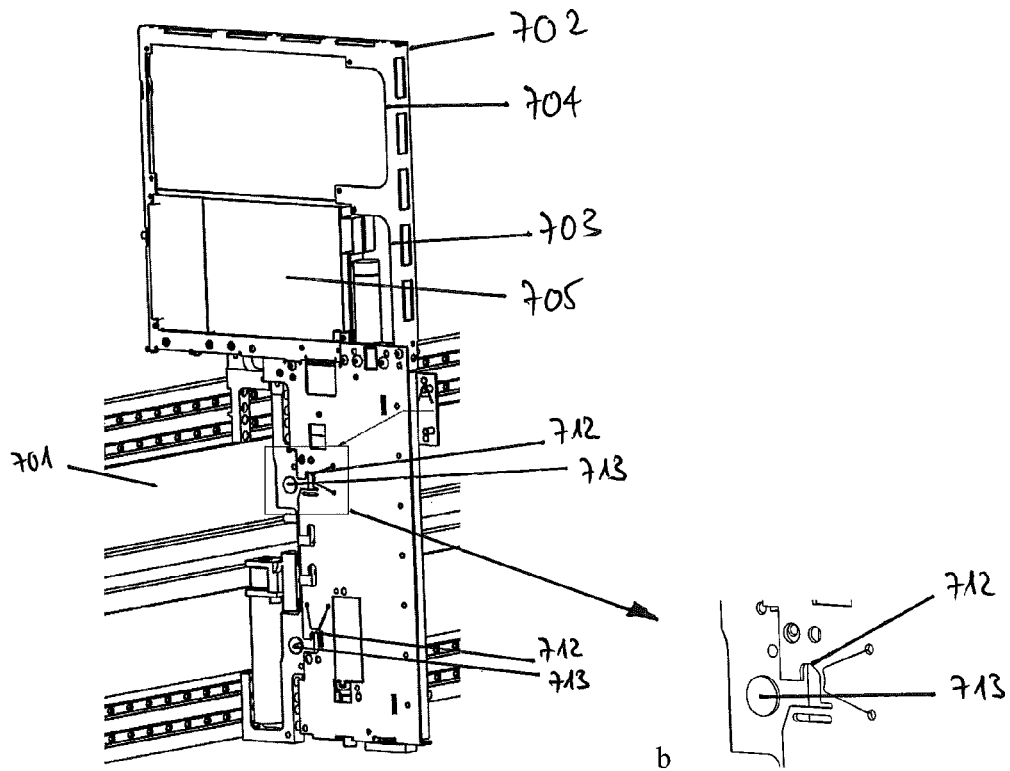
b
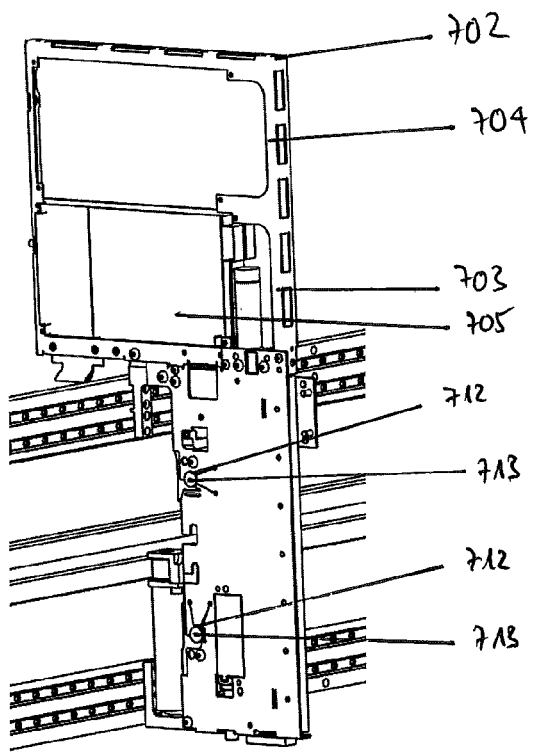
c

Fig. 7 a
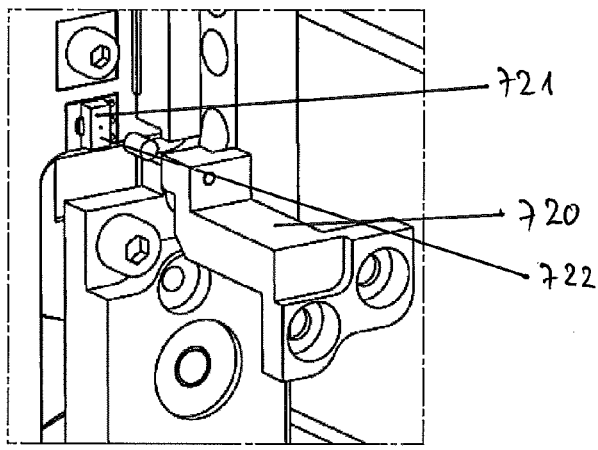
b
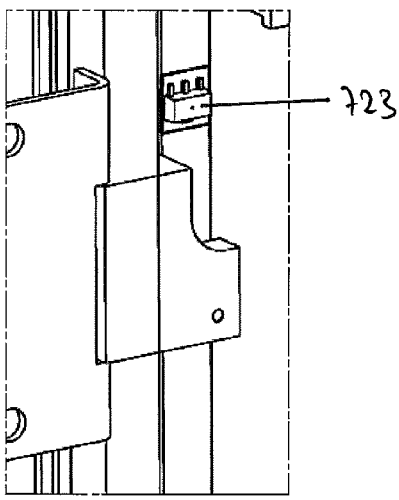
c
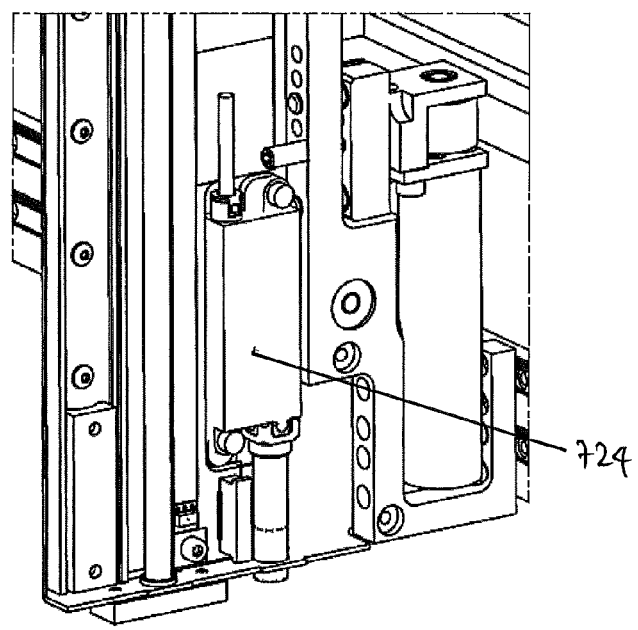

METHODS FOR USING A PIPETTING DEVICE WITH INDEPENDENTLY MOVABLE PIPETTE UNITS

CROSS-REFERENCES TO RELATED APPLICATIONS

The present application is a divisional of U.S. application Ser. No. 14/515,668 filed on Oct. 16, 2014, now U.S. Pat. No. 9,101,922, which is a divisional of U.S. application Ser. No. 13/169,593 filed on Jun. 27, 2011, now U.S. Pat. No. 8,900,527, which claims the benefit of priority under 35 U.S.C. §119 of EP10167646.8, filed Jun. 29, 2010, the contents of each are incorporated by reference herein in their entirety.

FIELD OF THE INVENTION

The present invention relates to a pipetting device, method and system with more than one pipetting units, wherein said pipetting units are movable relative to each other along one axis.

BACKGROUND OF THE INVENTION

Pipetting devices are used in automated analyzers for distributing samples or reagents. Pipetting devices comprising more than one pipetting unit are known in the art. Movable pipetting units are useful to transfer samples or reagents from one number of vessels to another number of vessels. Such a device with movable pipetting units is known from US2001/0036425.

The present invention provides an improved device with movable pipetting units.

SUMMARY OF THE INVENTION

The present invention relates to a device for aspirating and dispensing more than one liquid sample. The invention also relates to an analyzer comprising such a device. The device comprises a main frame body and more than one pipetting units, said pipetting units extending side by side in parallel with each other. A pipetting unit comprises an interface for interacting with an interface of a pipette tip. It further comprises a first module for aspirating and dispensing a liquid. One preferred embodiment of such a module is a pump (708). It further comprises a second module for Y-axis movement, and third module for Z-axis movement, wherein said second and third modules function independently. Said second and third modules are preferably actuators. More preferably, said third module is a spindle drive. Said pipette unit further comprises a fourth module for controlling functions of said pipette unit. Preferably, said fourth module is an electronic module controlling all functions of said pipette unit. The pipetting unit comprises two frames for receiving at least one of said modules, wherein said at least one module is mounted in one of said frames. Furthermore, the device comprises an X-transfer mechanism (719) connected to said main frame body to which said pipetting units are connected. Said at least one module of one pipette unit is mounted in one of said two frames, and said at least one module of the adjacent pipette units are mounted in the frame in the location corresponding to the frame of said first pipette unit which is empty.

The device according to the present invention has the advantage that an appropriate spacing between pipette units can be achieved even if modules required for each pipette unit are too broad to be placed next to each other.

BRIEF DESCRIPTION OF THE FIGURES

FIG. 1 shows two pipette units with staggered modules connected to a frame part.

FIG. 2 shows two pipette units moved into close proximity of each other.

FIG. 3 a) shows five pipette units connected to one frame part. Four pipette units are in close proximity, the fifth pipette unit is moved independently away from the others. In b) eight pipetting units are shown in close proximity to each other.

FIG. 5 a) to c) show the interface of frame parts with Y-carriage or fixed block.

FIG. 7 a) to c) show examples of sensors.

DETAILED DESCRIPTION OF THE INVENTION

Figure 4:
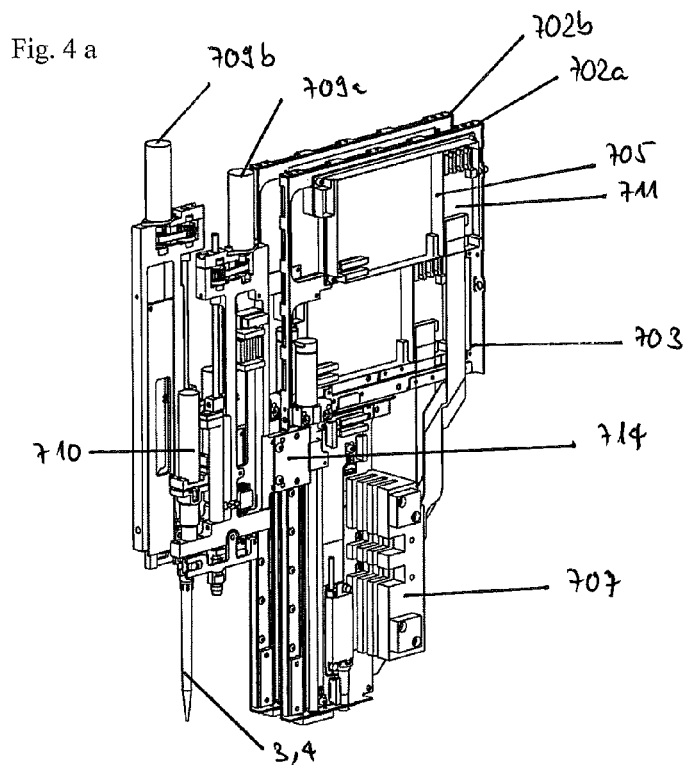
FIG. 4 shows a device with two units fixed to a support for movement in Z-direction, but not in Y-direction (a). In b) shows the two units from a) with individual parts separated.
Figure 4:
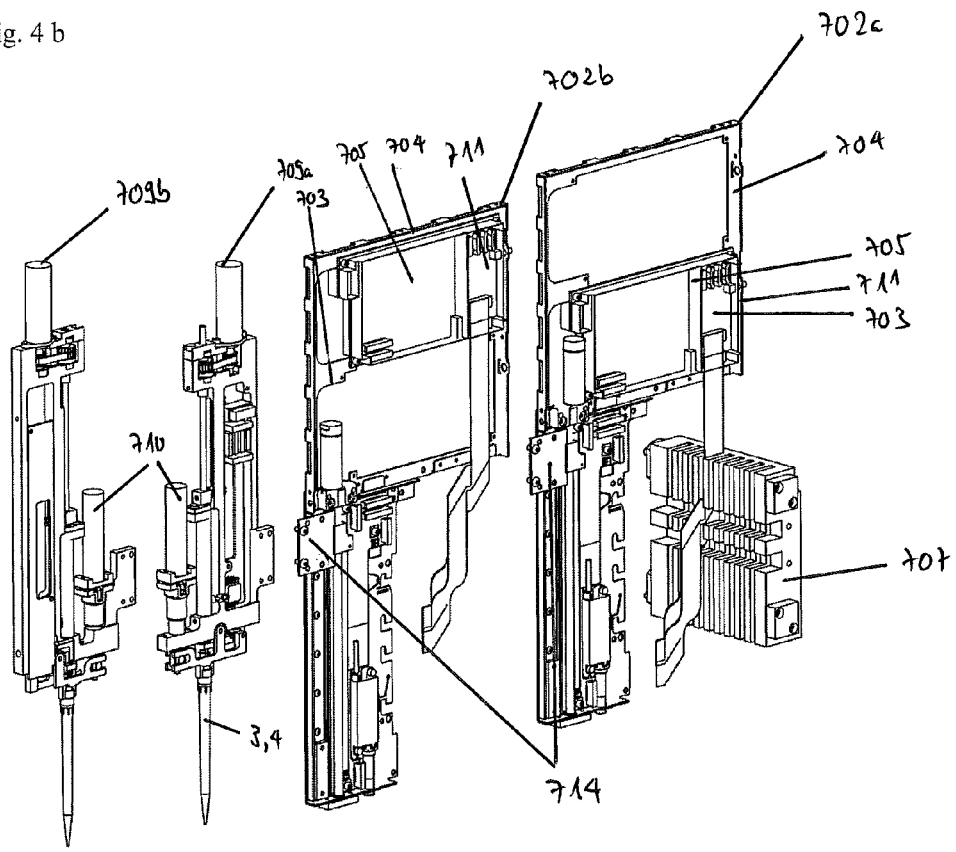

In one embodiment of the device hereinbefore described, at least one module is mounted outside of said frame, wherein the said modules of two adjacent pipetting units are staggered. This again allows achieving an appropriate spacing between said pipetting units. In another embodiment, the pipetting unit does not comprise frames. In this embodiment, at least one module is mounted in a staggered fashion on two adjacent pipetting units.

A preferred shortest distance between said more than one pipette units is 10 mm or shorter. More preferably, the shortest distance between said more than one pipette units is between 10 mm and 1 mm. Further preferred shortest distances are 9 mm, 4.5 mm, 2.25 mm, and 1.125 mm.

In a preferred embodiment, the device hereinbefore described additionally comprises a sixth module, which is a sensor module. Preferred sensor modules are sensors for initializing or determining the position in Y or Z direction of the pipette unit. Preferred sensors for determining the position of the pipette unit in is an ultrasound sensor.

Preferably, one side of a pipette unit is connected to said Y-axis transfer mechanism.

Preferably, said pipette units additionally comprise ball bearings, wherein said ball bearings of two adjacent pipette units are staggered.

The present invention further relates to a method of pipetting samples from a first set of vessels holding said samples to a second set of vessels, wherein the distance between adjacent vessels of the first set of vessels is different from the distance between adjacent vessels of the second set of vessels. Said method comprises aspirating said samples with pipette tips mounted on a device hereinbefore described, wherein the distance between said pipetting units is adjusted to the distance between said first set of vessels by moving the pipetting units along one axis prior to aspiration. The distance between the pipette units to the distance between said second set of vessels prior to dispensing is then adjusted for dispensing said samples into the second set of vessels.

In a preferred embodiment of the method hereinbefore described, said first set of vessels comprises at least two vessels in a linear arrangement. Preferably, said second set of vessels are integrally formed. In another preferred embodiment, the second set of vessels is only one vessel. In a more preferred embodiment, said second set of vessels comprises a multiwell plate.

The present invention further relates to a method of isolating and analyzing at least one analyte that may be present in at least one liquid sample in an automated analytical system, comprising the automated steps of providing a first set of vessels comprising said at least one liquid sample to said automated analytical system; aspirating at least a portion of said at least two liquid samples from said first set of vessels with a pipetting device comprising more than one pipetting unit, wherein the distance between said pipetting units is adjusted to the distance between the first set of vessels prior to aspiration; adjusting the distance between said pipetting units to the distance between vessels of a second set of vessels; dispensing said liquid samples into said second set of vessels. The method further comprises the steps of combining together a solid support material and one of said fluid samples in a well of said second set of vessels vessel for a period of time and under conditions sufficient to permit said analyte to be immobilized on the solid support material. Isolating the solid support material is then isolated from other material present in the fluid sample in a separation station. The analyte is then purified in the separation station by separating the fluid sample from the solid support material and washing the materials one or more times with a wash buffer. Finally, the analyte is analyzed. In a preferred embodiment, the method comprises at least two liquid samples. In another preferred embodiment, said analyte is a nucleic acid. More preferably, said device comprises the device hereinbefore described.

The present invention also relates to an analytical system for isolating an analyte, comprising a module for transferring samples from a first set of vessels to a second set of vessels, wherein said module comprises a pipetting device comprising more than one pipetting units, wherein said pipetting units are movable relative to each other along one axis; and a module for isolating said analyte. Preferably, said analytical system additionally comprises a module for analyzing said analyte.

A device (700) according to the invention comprising a main frame body (701) and two pipetting units (702a, b) is shown in FIG. 1. Each pipetting unit (702) comprises two frames (703, 704). In the non-limiting example shown in FIG. 1, any one of the pipetting unit (702) comprises an electronic module (705). The electronic module (705) of pipetting unit (702a) is mounted in the lower frame (703), the electronic module (705) of pipetting unit (702b) is mounted in the upper frame (704). The Y-axis actuators (717) are also mounted on the pipette units in a staggered fashion. The pipetting units also comprise interfaces (706) for interacting with pipette tips (3, 4).

FIG. 2 shows the two units (702a, b) as they are moved together, bringing the two pipette tips (3, 4) into close proximity. Corresponding modules (e.g., 705) are arranged in a non-overlapping way to allow for an optimal spacing between the two pipetting units. FIG. 3 a) shows a device (700) with five pipette units (702a to e) with the staggered mount of different modules (705). Four of the pipette units (702b to e) are shown with a short distance between each other. The fifth unit (702a) is shown in a position further away. FIG. 3b) shows a device (700) with eight pipetting units (702), wherein all units (702) are in close proximity to the adjacent units (702) and have needles (80) for pipetting.

FIG. 4 shows an embodiment of a pipetting device (700) which is only moved in Z-direction. a) Two units (702) are fixed in the support (707). To obtain a sufficiently small raster, e.g. a 9 mm raster, the units (702) are mounted in a staggered manner. Modules (710) on the tools (709) as well as modules (705, 711) on the frame part (703, 704) of the pipette unit (702) are staggered to obtain the required distance between the pipette units (702). b) Shows the pipette units (709a, b) and the frames (703, 704) in a disassembled manner.

FIG. 5 shows the interface to the frame body (701): a) the frame body is a Y-carriage; the pipetting unit (702) comprises an interacting part (712) which can be engaged with a receiving part (713) of the frame body (701) and releasably fixed. b) Shows a detail of the interacting part before engagement. c) Shows the frame engaged to the frame body.

Figure 6:
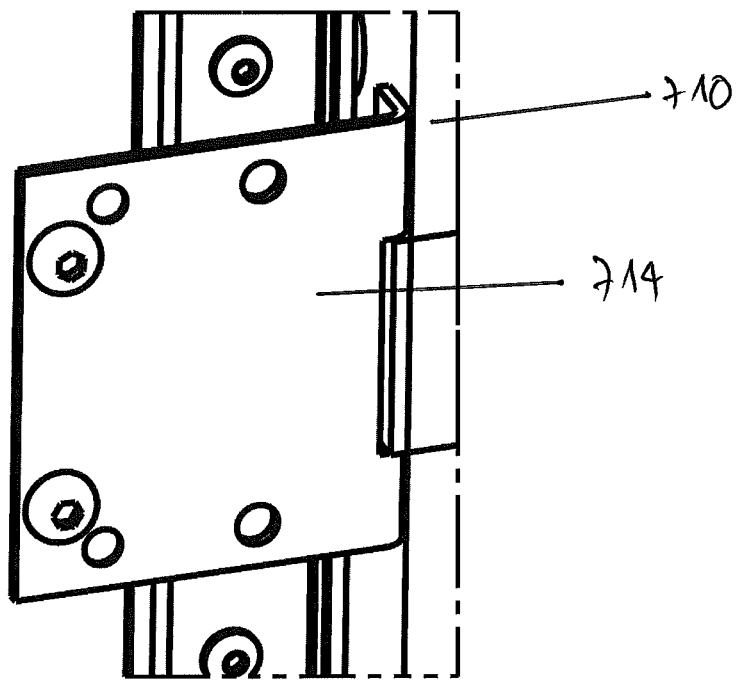
FIG. 6 shows an adapter plate (a) and the adapter plate with pipetting unit fixed to the frame part (b).
Figure 6:
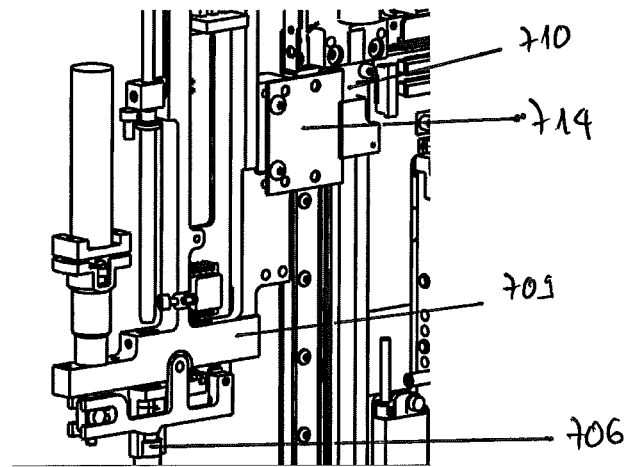

FIG. 6 a) shows an adaptor plate (714) for fixing the pipette tool (709) to the frame part (710) of the pipette unit (702). Other tools (715, 716) may also be attached to said frame part (710). b) Shows a detail of the pipette tool (709) fixed to the frame part (702).

The pipette unit may comprise additional modules. Preferably, such modules comprise sensors. Several types of sensors and other modules are shown in FIG. 7 a) to c), e.g., a magnet (720), a hallsensor (721), an init-sensor (723) of the Z-drive (718), an init sensor (722) of the Y-drive (717), an ultrasound sensor (724).

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method of isolating and purifying an analyte present in at least one liquid samples in an automated analytical system, comprising the automated steps of providing a first set of vessels comprising said samples to said automated analytical system;

aspirating at least a portion of said at least two liquid samples from said first set of vessels with a pipetting device comprising more than one pipetting unit, wherein a distance between said pipetting units is adjusted to the a first distance between the first set of vessels prior to aspiration;

adjusting the distance between said pipetting units to a second distance, different than the first distance, between vessels of a second set of vessels;

dispensing said liquid samples into said second set of vessels;

combining together a solid support material and liquid samples in said second set of vessels for a period of time and under conditions sufficient to permit said analyte to be immobilized on the solid support material;

isolating said analyte immobilized on the solid support material in a separation station; and purifying said analyte in the separation station by separating the solid support material from the liquid samples and washing the solid support material one or more times with a wash buffer wherein said analyte is a nucleic acid.

2. The method of claim 1, wherein said pipetting device comprises: a main body comprising a receiving part; two or more adjacent pipetting units extending vertically parallel to each other, each of said pipetting units comprising: an interacting part releasably engaging the receiving part of the main body in a fixed position; a pipette tip; an interface for interacting with an interface of the pipette tip; an upper frame and a lower frame each configured to receive and mount a module, at least one module present in the upper or lower frame of each pipetting unit, wherein the modules of two adjacent pipetting units are mounted in a staggered fashion between the upper frame of one of the two or more adjacent pipetting units, and the lower frame of a second adjacent pipetting unit; and an X-transfer mechanism connected to said main body to which said two or more adjacent pipetting units are connected.

3. The method of claim 2, wherein said modules comprise at least one of: a pump for aspirating and dispensing a liquid; a Y-axis actuator, and a Z-axis actuator, wherein said Y-axis actuator and said Z-axis actuator function independently; or an electronic module for controlling functions of said two or more pipetting adjacent units.

\* \* \* \* \*